US00PP14469P39

(12) United States Plant Patent
Pieters

(10) Patent No.: US PP14,469 P3
(45) Date of Patent: Jan. 20, 2004

(54) CHRYSANTHEMUM PLANT NAMED 'GEDI TWO YLPAP'

(50) Latin Name: *Chrysanthemum morifolium*
Varietal Denomination: Gedi Two Ylpap

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/138,117

(22) Filed: May 1, 2002

(65) Prior Publication Data

US 2003/0208825 P1 Nov. 6, 2003

(51) Int. Cl.[7] ..... A01H 5/00

(52) U.S. Cl. ..... Plt./295
(58) Field of Search ..... Plt./295, 286

(56) References Cited

U.S. PATENT DOCUMENTS

PP11,725 P 12/2000 Pieters ..... Plt./295

*Primary Examiner*—Bruce R. Campbell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a daisy-type inflorescence, consistent flowering response to short days, blooming consistently after 46 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Ylpap'.

BACKGROUND OF THE INVENTION

The new cultivar is a product of a naturally occurring mutation on a single branch of the variety 'Papiro' (U.S. Plant Pat. No. 12,998). The new cultivar was discovered in cultivation and selected by the inventor in October 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Ylpap' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Ylpap'. These characteristics in combination distinguish 'Gedi Two Ylpap' as a new and distinct Chrysanthemum cultivar:

1. Daisy-type inflorescence,
2. Consistent flowering response to short days, blooming consistently after 46 days of short day length,
3. Free branching habit,
4. Yellow ray florets, 5. Very uniform round growth habit, and
6. Large quantity of blooms per flowering branch.

Plants of the new cultivar are similar to plants of the parent cultivar, 'Papiro' in most horticultural characteristics, however plants of the new cultivar differed from plants of the cultivar 'Papiro' primarily in ray floret color.

In comparison to the commercially available variety 'Gedi YT8' (U.S. Plant Pat. No. 11,725), 'Gedi Two Ylpap' has longer lateral branches, a lighter yellow ray floret color, and more blooms per flowering branch. In addition, no pollen has been detected in observations of the new cultivar.

BRIEF DESCRIPTION OF THE PHOTOGRAPH

The photograph shows a plant of 'Gedi Two Ylpap' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 71 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Ylpap'.

Commercial classification: Garden-type Chrysanthemum.

Parentage: Naturally occurring mutation on a single branch of the variety 'Papiro' (U.S. Plant Pat. No. 12,998).

PROPAGATION

Time to rooting: 7 to 14 days at approximately 21° C.
Root description: Fine, fibrous.

PLANT

Growth habit: Mounding herbaceous perennial.
Height: Approximately 22.5 cm.
Spread: Approximately 25 cm.
Growth rate: Moderate.
Branching characteristics: Free Branching.
Length of lateral branches: Approximately 20 cm.
Number of leaves per lateral branch: Approximately 13.

FOLIAGE

Leaf:
- *Arrangement.*—Alternate.
- *Average length.*—Approximately 5.3 cm.
- *Average width.*—Approximately 4.2 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 137C. Mature foliage upper side: Near 139A. Mature foliage under side: Near 137B. Venation upper side: Near 139C. Venation under side: Near 138B.
- *Venation type.*—Palmately net.

Petiole:
- *Average length.*—Approximately 2.7 cm.
- *Color.*—Near 139A.
- *Diameter.*—Approximately 0.3 cm.

BLOOM

Inflorescence:
- *Flowering habit.*—Induced by darkness period greater than 13.5 hours, approximately 46 days of appropriate day length required to induce and develop blooms.
- *Inflorescence form.*—Daisy.
- *Natural flowering season.*—Approximately between the last 10 days of September through the first 9 days of October.
- *Number of inflorescences per lateral branch.*—Approximately 29.
- *Inflorescence diameter.*—Approximately 4.6 cm.
- *Inflorescence depth.*—Approximately 1.3 cm.
- *Inflorescence longevity on plant.*—Approximately 28 days.
- *Persistence.*—Persistent.
- *Disc diameter.*—Approximately 1.4 cm.

Ray florets:
- *Appearance.*—Matte.
- *Texture.*—Smooth.
- *Average number per flower.*—39.
- *Shape.*—Oblong.
- *Aspect.*—Flat.
- *Margin.*—Entire.
- *Apex.*—Rounded.
- *Length.*—Approximately 2.2 cm.
- *Width.*—Approximately 0.7 cm.
- *Color.*—Upper surface at first opening: Near 4B. Upper surface at maturity: Near 4B. Upper surface at fading: Near 4C. Under surface at first opening: Near 4C. Under surface at maturity: Near 4C. Under surface at fading: Near 4D.

Disc florets:
- *Appearance.*—Shiny.
- *Texture.*—Smooth.
- *Average number per flower.*—Approximately 112.
- *Shape.*—Cylindric.
- *Apex.*—Obtuse.
- *Average length.*—Approximately 0.4 cm.
- *Average width.*—Approximately 0.1 cm.
- *Color.*—At first opening: Near 154A. At maturity: Near 6A. At fading: Near 7A.

Peduncle:
- *Length.*—At terminal end (shortest): Approximately 3.1 cm. At lateral end (longest): Approximately 10.5 cm.
- *Angle to stem.*—Acute.
- *Strength.*—Moderate.
- *Color.*—Near 138A.
- *Habit.*—Upright.
- *Diameter.*—Approximately 0.2 cm.
- *Surface texture.*—Lightly pubescent.

Inflorescence bud:
- *Length.*—Approximately 0.5 cm.
- *Diameter.*—Approximately 0.8 cm.
- *Form.*—Globular.
- *Color.*—Near 138A.

Involucral bracts (phyllaries):
- *Appearance.*—matte.
- *Texture.*—Lightly pubescent.
- *Number.*—21.
- *Shape.*—Oblanceolate.
- *Margin.*—Entire.
- *Apex.*—Rounded.
- *Length.*—Approximately 0.6 cm.
- *Width.*—Approximately 0.3 cm.
- *Color.*—Upper side: Near 143A. Under side: Near 143A.

REPRODUCTIVE ORGANS

Ray florets:
- *Number of pistils per flower.*—1.
- *Stigma shape.*—2 branched.
- *Stigma color.*—Near 5A.
- *Style color.*—Near 154D.
- *Style length.*—Approximately 0.4 cm.
- *Stamens.*—Absent.

Disc florets:
- *Number of pistils per flower.*—1.
- *Stigma shape.*—Two-branched.
- *Stigma color.*—Near 12A.
- *Style length.*—Approximately 0.3 cm.
- *Style color.*—Near 154D.
- *Number of stamens per flower.*—4.
- *Anther shape.*—Tubular.
- *Anther color.*—Near 15A.
- *Pollen color.*—Near 15C.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2 C. Non flowering plants are hardy in the approximate range of 3 C. to −6 C., depending upon duration of cold and amount of moisture in the soil. With adequate water plants are hardy to a high temperature of 49 C.

What is claimed is:

1. A new and distinct cultivar of Chrysanthemum plant named 'Gedi Two Ylpap' as herein illustrated and described.

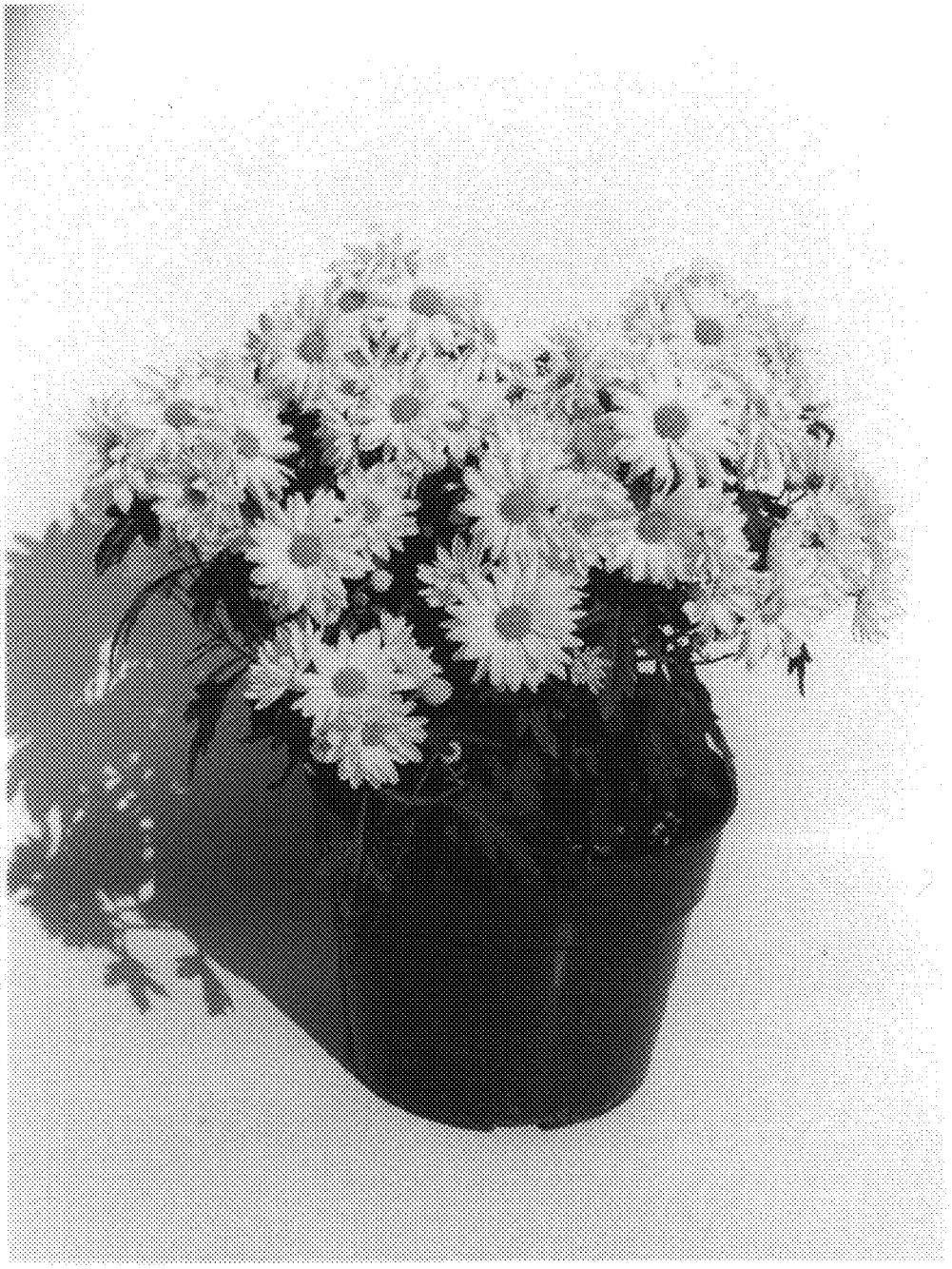

* * * * *